United States Patent
Rey et al.

(10) Patent No.: US 6,495,711 B2
(45) Date of Patent: Dec. 17, 2002

(54) PROCESS FOR PREPARING (−)-(1S, 4R) N-PROTECTED 4-AMINO-2-CYCLOPENTENE-1-CARBOXYLATE ESTERS

(75) Inventors: Max Rey, Wallisellen (CH); Gregor Welti, Zurich (CH); Cynthia Maryanoff, Forest Grove, PA (US)

(73) Assignee: BioCryst Pharmaceuticals Inc., Birmingham, AL (US)

( * ) Notice: Subject to any disclaimer, the term of this patent is extended or adjusted under 35 U.S.C. 154(b) by 0 days.

(21) Appl. No.: 10/020,402

(22) Filed: Dec. 18, 2001

(65) Prior Publication Data

US 2002/0052524 A1 May 2, 2002

Related U.S. Application Data

(63) Continuation of application No. 09/590,852, filed on Jun. 9, 2000, now abandoned.
(60) Provisional application No. 60/141,292, filed on Jun. 28, 1999.

(51) Int. Cl.$^7$ .................. C07C 261/00; C07C 69/74; C07C 61/06; C07C 229/00; C07C 59/255
(52) U.S. Cl. .................. 560/115; 560/122; 560/125; 560/126; 560/128; 562/504; 562/507; 562/508; 562/510; 562/582; 562/585
(58) Field of Search ................. 560/115, 122, 560/125, 126, 128; 562/504, 507, 508, 510, 582, 585

(56) References Cited

U.S. PATENT DOCUMENTS

| | | |
|---|---|---|
| 5,034,394 A | 7/1991 | Daluge |
| 6,410,594 B1 | 6/2002 | Babu et al. |

FOREIGN PATENT DOCUMENTS

| | | |
|---|---|---|
| EP | 0424064 A1 | 4/1991 |
| EP | 0424064 B1 | 4/1991 |
| EP | 0590685 A1 | 4/1994 |
| EP | 0590685 B1 | 4/1994 |
| WO | 99/33781 * | 7/1999 |

OTHER PUBLICATIONS

Steven J. C. Taylor et al., Journal Chemical Soc., Chem. Commun., 1990, pp. 1120–1121, Chemoenymatic Synthesis of (−)–Carbovir Utilizing a Whole Cell Catalysed Resolution of 2–Azabicyclo[2.2.1]HEPT–5–EN–3–One.
Sames Sicsic et al., Tetrahedron Lett., vol. 28, No. 17, Jul. 1987 pp. 1887–1888, Chemoenzymatic Approach to Carbocyclic Analogues of Ribonucleosides and Nicotinamide Ribose.
Calvin A. Buehler et al., Wiley–Interscience, 1970, pp. 818, 824, Organic Synthesis.
Ernest L. Eliel, McGraw–Hill Book Co., 1962, pp. 46–52, Stereochemistry of Carbon Compounds.
Tetsuji Kametani et al., Tetrahedron, 1981, vol. 37, pp. 715–719, Studies of the Synthesis of Heterocyclic Compounds–DCCLXII.

* cited by examiner

Primary Examiner—J. Parsa
(74) Attorney, Agent, or Firm—Connolly Bove Lodge & Hutz LLP

(57) ABSTRACT

The invention relates to a process for preparing (−)-(1S,4R) N protected 4-amino-2-cylcopentene-1-carboxylate esters represented by the formula (I)

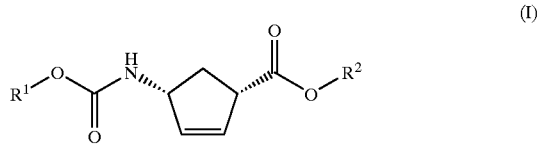

wherein $R^1$ and $R^2$ are as described within the specification.

19 Claims, No Drawings

PROCESS FOR PREPARING (−)-(1S, 4R) N-PROTECTED 4-AMINO-2-CYCLOPENTENE-1-CARBOXYLATE ESTERS

CROSS REFERENCE TO RELATED APPLICATIONS

This application claims the benefit of U.S. Provisional Application No. 60/141,292, filed on Jun. 28, 1999, which is a continuation of Ser. No. 09/590,852 filed Jun. 9, 2000 now is abandoned.

BACKGROUND OF THE INVENTION

Field of the Invention

The invention relates to a process for preparing (−)-(1S, 4R) N-protected 4-amino-2-cylcopentene-1-carboxylate esters represented by the formula (I):

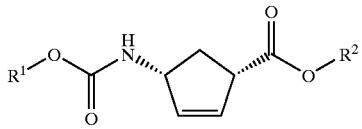

wherein
$R^1$ and $R^2$ are independently selected from the group consisting of hydrogen, alkyl, cycloalkyl, aryl and aralkyl.

Compounds of formula (I) are useful as an intermediate in the synthesis of a substituted cyclopentane derivatives described in pending application PCT US 98/26871, filed Dec. 17, 1997. The substituted cyclopentane derivatives described in pending application PCT US 98/26871 inhibit influenza virus neuramidase and are thus useful in the treatment and/or prevention of influenza virus infection.

Known methods for preparing the compounds of formula (I) are disclosed in pending application PCT US 98/26871, filed Dec. 19, 1997.

A known method for the preparation of cis-4-aminocyclopent-2-ene-1-carboxylic acid using enzymatic resolution of the (±)2-Azabicyclo[2.2.1]hept-5-en-3-one (±)lactam is disclosed by Taylor, J. C., et al. JCS Chem Commun. 1990, 1120 (EP 424064). Similarly, the enzymatic resolution of (±)-cis-Methyl 4-acetamidocyclopent-2-ene carboxylate using pig liver esterase is disclosed by Sicsic, J. et al., Tetrahedron Lett. 1987, 28, 1887. The use of enzymes, however, makes these processes impractical for large scale production.

A method for classical resolution of (±)-cis-4-benzamidocyclopent-2-ene carboxylic acid with (+)-cis-2-(benzylamino) cyclohexanemethanol is disclosed in EP 590685 (Nohira, H., et al.). Classical resolution of (±)-4-aminocyclopent-2-ene-1-methanol using dibenzoyl-D-tartaric acid is disclosed in U.S. Pat. No. 5,034,394 (S. M. Daluge). Application of classical resolution techniques to large scale production of compounds of formula (I) is not practical due to cost and availability of reagents.

Thus, there exists a need for resolution of the enantiomers of (−)-(1S,4R) N-protected 4-amino-2-cyclopentene-1-carboxylare esters of the formula (I) in high chemical yield and high enantiomeric purity.

SUMMARY OF THE INVENTION

The invention relates to a process of preparing a compound of formula (I)

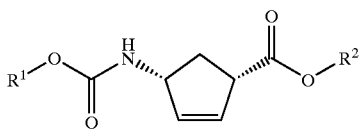

wherein
$R^1$ and $R^2$ are independently selected from the group consisting of hydrogen, alkyl, cycloalkyl, aryl, substituted aryl and aralkyl;

comprising

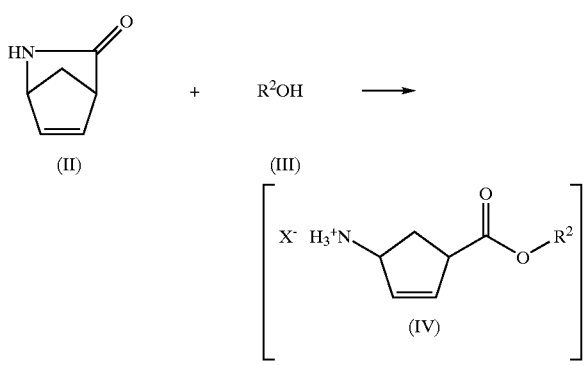

reacting (±)2-azabicyclo[2.2.1]hept-5-en-3-one of formula (II) with an alcohol of formula (III), and a non-aqueous acid, to form the corresponding Compound of formula IV, wherein X is the corresponding acid anion;

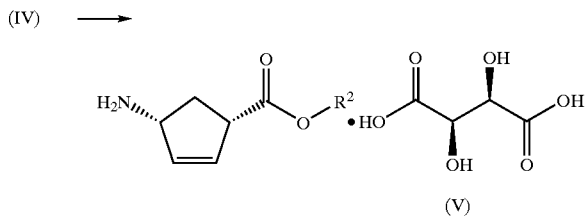

reacting the Compound of formula (IV) with L-tartaric acid and a tertiary amine, to form the corresponding Compound of formula (V);

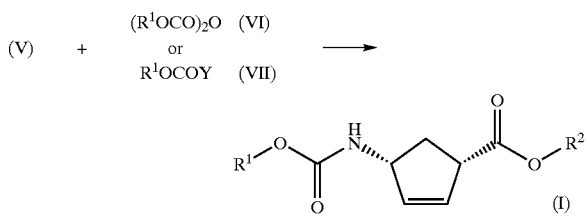

suspending the Compound of formula (V) in an organic solvent and treating with a Compound of formula (VI) or a Compound of formula (VII), wherein Y is chlorine or bromine and wherein $R^1$ is as set forth above, in the presence of a base, to form the corresponding Compound of formula I.

In another embodiment of the invention, the Compound of formula (I) is prepared by resolution of the Compound of formula (IV) with D-tartaric acid, followed by treatment with L-tartaric acid.

DETAILED DESCRIPTION

As used herein, the term "alkyl" whether used alone or as part of a substituent group, include straight and branched chains of one to eight carbon atoms, preferably one to three carbon atoms. For example, alkyl radicals include methyl, ethyl, propyl, isopropyl, butyl, isobutyl, sec-butyl, t-butyl, pentyl and the like.

As used herein, unless otherwise noted, "cycloalkyl" shall denote a monocyclic, saturated ring structure containing three to eight carbon atoms. Suitable examples of cycloalkyl groups include cyclopropyl, cyclobutyl, cyclopentyl, cyclohexyl, and the like.

As used herein, unless otherwise noted, "aryl" shall refer to unsubstituted carbocyclic aromatic groups such as phenyl, naphthyl, and the like, preferably phenyl.

As used herein, unless otherwise noted, "aralkyl" shall mean any $C_1$–$C_6$ alkyl group substituted with an aryl group. Suitable examples of aralkyl groups include benzyl, phenylethyl, and the like.

As used herein, unless otherwise noted, substituents on the aryl, and aralkyl groups are one or more, preferably one to two substituents, of halogen.

With reference to substituents, the term "independently" means that when more than one of such substituents is possible, such substituents may be the same or different from each other.

Examples of "non-aqueous acid" useful in the present invention include, but are not limited to gaseous hydrochloric, gaseous hydrobromic, p-toluenesulfonic, sulfuric, perchloric, tetrafluoroboronic, methanesulfonic, and the like.

As used herein, the notation "*" shall denote the presence of a stereogenic center.

Where the compounds of the invention contain one stereogenic center, they exist as enantiomers. Where the compounds contain two or more stereogenic centers, they exist as diastereomers. It is to be understood that all such isomers and mixtures thereof are encompassed within the scope of the present invention.

In a preferred embodiment of the invention, the claimed process is used to prepare a Compound of formula (I) wherein $R^1$ is tert-butyl and $R^2$ is methyl.

The present invention relates to a process for preparing a compound of formula (I) as outlined in Scheme 1, below:

Scheme 1

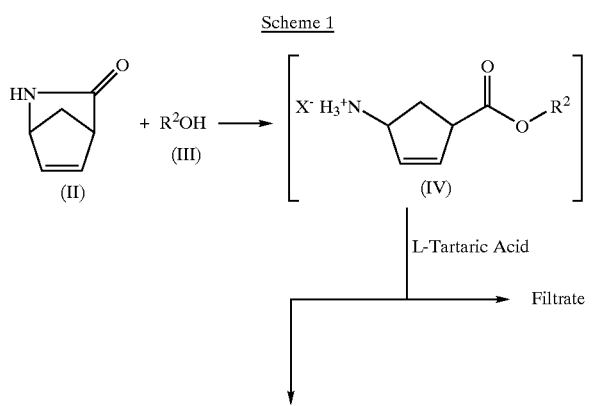

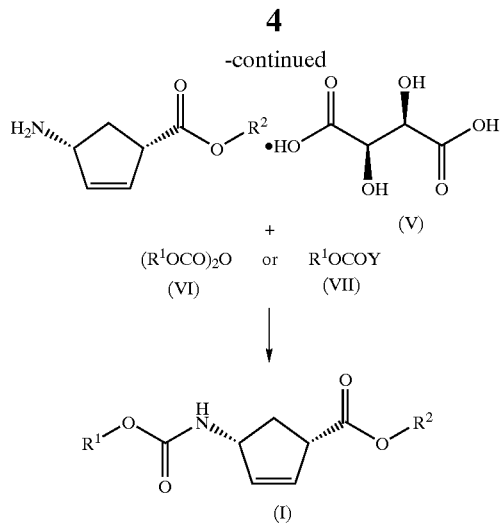

wherein $R^1$, $R^2$, X and Y are as described above.

More particularly, a compound of formula (II), a known compound, is reacted with an alcohol of formula (III), a known compound or compound prepared by known methods, and a non-aqueous acid, preferably gaseous hydrochloric, preferably at a temperature of less than or equal to about 75° C., more preferably at a temperature in the range of about 65–70° C., to form the corresponding Compound of formula (IV).

The solution containing the Compound of formula (IV) is preferably cooled to between about 15–50° C., more preferably to between about 20–25° C., reacted with L-tartaric acid, in an amount in the range of 0.4–2.2 eq, preferably in an amount in the range of about 0.5–0.6 eq, and preferably treated with water. The resulting solution is treated with a tertiary amine such as triethylamine, diisopropyl ethylamine, N-methyl morpholine, and the like, preferably triethylamine, in an amount sufficient to adjust the pH to between about 1–7, preferably to a pH between about 1–5, preferably the temperature is maintained in the range as set forth above, and preferably seeded with the compound of formula (V), to form the corresponding Compound of formula (V). Alternatively, the solution containing the Compound of formula (IV) is treated with a mixture of the L-tartaric acid, water and tertiary amine, to form the corresponding Compound of formula (V).

The Compound of formula (V) is suspended in an organic solvent such as ethyl acetate, an alcohol of formula (III), and the like, preferably an alcohol of formula (III), and reacted with a Compound of formula (VI), $(R^1OCO)_2O$, or a Compound of formula (VII), $R^1OCOY$, wherein Y is chlorine or bromine, in the presence of a base such as sodium carbonate, potassium carbonate, triethylamine, diisopropyl ethylamine, N-methyl morpholine, and the like, preferably triethylamine, preferably in an amount equal to at least 2 equivalents, preferably at a temperature in the range of about 25–35° C., to form the corresponding compound of formula (I).

The compound of formula (I) is isolated by known methods, for example by adding water and seeding or by recrystallization.

A further aspect of the invention is a process for preparing the Compound of formula (I) as outlined in Scheme 2, below:

SCHEME 2

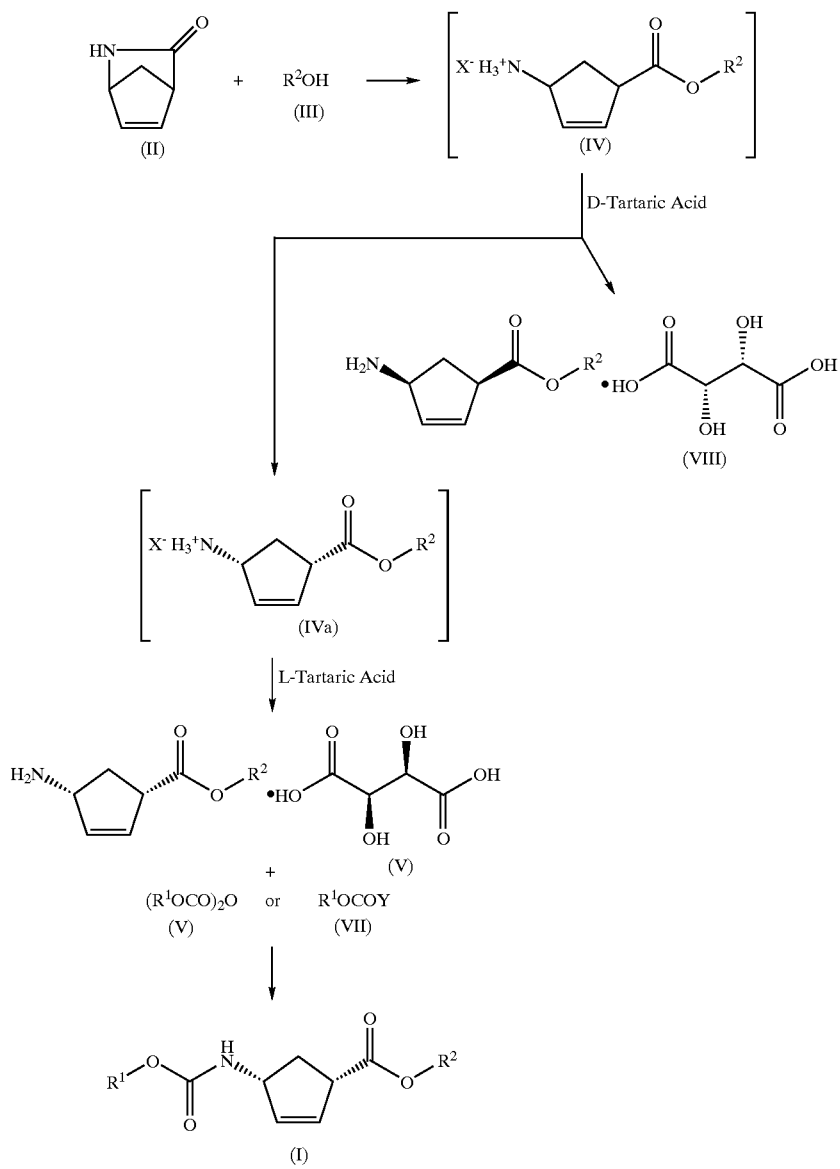

wherein $R^1$, $R^2$, X and Y are as described above.

More particularly, a compound of formula (II) is reacted with an alcohol of formula (III), and a non-aqueous acid, preferably gaseous hydrochloric, preferably at a temperature of less than or equal to about 75° C., more preferably at a temperature in the range of about 65–70° C., to form the corresponding Compound of formula (IV).

The solution containing the Compound of formula (IV) is preferably cooled to a temperature of between about 15–50° C., more preferably to a temperature between about 20–25° C., reacted with D-tartaric acid, in an amount in the range of 0.4–2.2 eq, preferably in an amount in the range of about 0.5–0.6 eq, and preferably treated with water. The resulting solution is treated with a tertiary amine such as triethylamine, diisopropyl ethylamine, N-methyl morpholine, and the like, preferably triethylamine, in an amount sufficient to adjust the pH to between about 1–7, preferably to a pH between about 1–5, preferably the temperature is maintained in the range as set forth above, and preferably seeded with compound of formula (VIII) to form the corresponding Compound of formula (VIII).

The compound of formula (VIII) is collected by filtration.

The filtrate, containing the compound of formula (IVa), is treated with L-tartaric acid, in an amount in the range of 0.5–1.2 eq, preferably in an amount in the range of 0.5–0.6 eq. The resulting solution is treated with a tertiary amine such as triethylamine, diisopropyl ethylamine, N-methyl morpholine, and the like, preferably triethylamine, in an amount sufficient to adjust the pH to between about 1–7, preferably to a pH between about 1–5, preferably the temperature is maintained in the range of about 15–50° C., more preferably in the range of 20–25° C., and preferably seeded with the compound of formula (V) to form the corresponding Compound of formula (V). Alternatively, the filtrate containing the Compound of formula (IV) is treated with a mixture of the L-tartaric acid, water and tertiary amine, to form the corresponding Compound of formula (V).

The Compound of formula (V) is suspended in an organic solvent such as ethyl acetate, an alcohol of the formula (III), and the like, preferably an alcohol of formula (III), and reacted with a Compound of formula (VI), (R$^1$OCO)$_2$O, or a Compound of formula (VII), R$^1$OCOY, wherein Y is chlorine or bromine, in the presence of a base such as sodium carbonate, potassium carbonate, triethylamine, diisopropyl ethylamine, N-methyl morpholine, and the like, preferably triethylamine, preferably in an amount equal to at least 2 equivalents, preferably at a temperature in the range of about 25–35° C., to form the corresponding compound of formula (I).

The compound of formula (I) is isolated by known methods, for example by adding water and seeding or by recrystallization.

The following examples are intended to illustrate the invention but not to limit it.

EXAMPLE 1

(1S,4R) Methyl 4-aminocyclopent-2-ene-1-carboxylate L-tartrate &

(1R,4S) Methyl 4-aminocyclopent-2-ene-1-carboxylate D-tartrate (±)-2-Azabicyclo[2.2.1]hept-5-en-3-one (100.0 g, 0.916 mol) was dissolved (endothermic) in methanol (83.0 g) to give a brown solution. HCl gas (37.8 g, 1.035 mol) was carefully introduced over 20 min. The induced reaction was exothermic causing the reaction mixture to reflux. After complete addition of HCl, the mixture was cooled to 20–25° C. L-Tartaric acid (82.5 g 0.55 mol) and water (50.0 g) were added in turn. The reaction solution became dark brown and the pH decreased. Triethylamine (60.3 g, 0.596 mol) was then added over 30 min. During the addition, the temperature was maintained below 50° C. When the pH of the solution reached 1.8–2.0 a few crystals of (1S,4R) Methyl 4-aminocyclopent-2-ene-1-carboxylate L-tartrate were added as seeds. The mixture was cooled to 22–25° C. and filtered. The solid was washed with methanol (80.0 g) and dried at 40° C. under vacuum (<50 mbar).

Yield: L-tartaric acid salt of (1S,4R) Methyl-4-aminocyclopent-2-ene-1-carboxylate (112.0 g, 83%, ee≧99% with HPLC); mp: 174.3–174.9° C.; [α]$_D^{20° C.}$=−40.4° (c=1 g/dL, H$_2$O).

To the mother liquor was added D-tartaric acid (123.8 g, 0.825 mol), (pH 1.5). Triethylamine (83.5 g, 0.825 mol) was then added over 30 min. During the addition, the temperature of the solution increased from 20° C. to about 45° C., but was not allowed to increase above 50° C. The precipitate was filtered and washed with methanol (80.0 g). The solid was dried at 40° C. under vacuum (<50 mbar).

Yield: (1R,4S)-Methyl 4-aminocyclopent-2-ene-1-carboxylate D-tartrate (122.2 g, 91%, ee≧99.5% with HPLC); mp: 174.9–175.4° C.; [α]$_D^{2° C.}$=+40.8° (c=1 g/dL, H$_2$O).

EXAMPLE 2

(1R, 4S)-Methyl-4-aminocyclopent-2-ene-1-carboxylate D-tartrate &

(1S, 4R)-Methyl-4-aminocyclopent-2-ene-1-carboxylate L-tartrate (±)-2-azabicyclo[2.2.1]hept-5-ene-3-one (100.0 g, 0.1916 mol) was dissolved in methanol (83.0 g). HCl gas (37.8 g, 1.035 mol ) was introduced over 20 min. The induced reaction was exothermic causing the reaction mixture to reflux. After complete addition of HCl, the mixture was cooled to 20–25° C. D-Tartaric acid (82.5 g, 0.55 mol) and water (50.0 g) were added in turn. The reaction solution became dark and the pH decreased to pH<0. Triethylamine (60.3 g, 0.596 mol) was added over 30 min. During the addition, the temperature was maintained below 50° C. When the pH of the solution reached 1.8–2.0 a few crystals of (1R, 4S)-Methyl-4-aminocyclopent-2-ene-1-carboxylate D-tartrate were added as seeds. The mixture was cooled to 22–25° C. and filtered. The solid was washed with methanol (80.0 g) and dried at 40° C. under vacuum (<50 mbar).

Yield: (1R, 4S)-Methyl-4-aminocyclopent-2-ene-1-carboxylate D-tartrate (112.1 g, 83%, ee≧99% with HPLC).

To the filtrate was added L-tartaric acid, (123.8 g, 0.825 mol). Triethylamine (83.5 g, 0.825 mol) was then added over 30 min. During the addition, the temperature of the solution increased from 20° C. to about 45° C., but was not allowed to increase above 50° C. The precipitate was filtered and washed with methanol (80.0 g). The solid was dried at 40° C. under vacuum (<50 mbar).

Yield: (1S, 4R)-Methyl-4-aminocyclopent-2-ene-1-carboxylate L-tartrate (122.0 g, 91%, ee≧99.5% with HPLC).

EXAMPLE 3

(1S,4R) Methyl 4-[[(1,1,-dimethylethoxy)carbonyl]amino]-2-cyclopentene-1-carboxylate from (1S,4R) Methyl 4-aminocyclopent-2-ene-1-carboxylate L-tartrate (1S,4R)-Methyl 4-aminocyclopent-2-ene-1-carboxylate L-tartrate (100.0 g, 0.343 mol) and di-tert-butyl carbonate (78.7 g, 0.361 mol) were suspended in methanol (130.0 g). Triethylamine (80.0 g, 0.791 mol) was added to the suspended solution, at 30–35° C. Following addition of approximately half of the amine, the mixture turned into a solution and gas evolution (CO$_2$) started. After complete addition of the amine, the solution was stirred for 1 h without heating. The solution was cooled to 5–10° C. and water (375 ml) was added over 10–15 min. A few crystals of (1S,4R) 4-[[(1,1,-dimethylethoxy)carbonyl]amino]-cyclopent-2-ene-1-carboxylate were added as seeds to yield a white precipitate. The mixture was stirred for 2 h at 5–10° C. and then filtered. The solid was washed with water (50 ml) and dried at 35–40° C. under vacuum (<50 mbar).

Yield: (1S,4R) 4-[[(1,1,-dimethylethoxy)carbonyl]amino] cyclopent-2-ene-1-carboxylate (79.0 g, 95.7%); mp: 51.9–52.4° C.; [α]$_D^{20° C.}$=−52.0° (c=1 g/dL, H$_2$O).

EXAMPLE 4

Isolation of (1S,4R) Methyl 4-aminocyclopent-2-ene-1-carboxylate from its L-tartrate Salt (1S,4R)-Methyl 4-aminocyclopent-2-en-1-carboxylate L-tartrate (5 g, 17.2 mmol) in methanol (6.0 g) was treated with methylamine (4.3 mL, 34.5 mmol) in ethanol (8M). After addition of about half of the methylamine base, a solution was formed. Further addition resulted in precipitation of the tartaric acid as its corresponding di(methylammonium) salt. The solutioin was filtered to yield (1S,4R) Methyl 4-aminocyclopent-2-ene-1-carboxylate, containing only a trace of tartaric acid.

EXAMPLE 5

Isolation of (1S,4R) Methyl 4-aminocyclopent-2-ene-1-carboxylate Hydrochloride from its L-tartrate Salt To a mixture of (1S,4R)-Methyl 4-aminocyclopent-2-ene-1-carboxylate L-tartrate (10 g, 34.3 mmol) and ammonium chloride (1.85 g, 34.3 mmol) in ethanol (79 g) was added a 2M solution of ammonia in methanol (17.2 mL, 34.4 mmol). The mixture was stirred for 2 h, resulting in precipitation of the tartaric acid di-ammonium salt. The solid was removed by filtration and the filtrate was concentrated to about 10 mL. The concentrated filtrate was diluted with methyl isobutyl ketone (MIK), resulting in precipitation of (1S,4R) Methyl-4-aminocyclopent-2-ene-1-carboxylate hydrochloride. The solid was collected by filtration and dried in a vacuum oven (100 mbar) at 50° C. for 24 h.

Yield: 5.06 g, 83%; $[\alpha]_D^{20°C.}$=–90.5° (c=1 g/dL, MeOH);

$^1$H NMR (D$_2$O) δ 6.20–6.17 (m, 1H), 5.97–5.94 (m, 1H), 4.40–4.30 (m, 1H), 3.80–3.71 (m, 1H), 3.72 (s, 3H), 2.72–2.52 (m, 1H), 2.12–2.00 (m, 1H). $^{13}$C NMR (D$_2$O) δ 176.0 (C), 135.8 (CH), 129.6 (CH), 51.6 (CH), 52.8 (CH), 49.5 (CH$_3$), 31.1 (CH$_2$).

EXAMPLE 6

(1S,4R) Methyl 4-[[(1,1,-dimethylethoxy)carbonyl]amino]-2-cyclopentene-1-carboxylate Step 1:

(±)-2-Azabicyclo[2.2.1]hept-5-en-3-one (240 g, 2.2 mol) was dissolved in methanol (230 g) by slightly heating to 20° C. Hyflo Super Cel® (4.8 g) was added to the resulting dark brown solution. The suspension was filtered and the filter cake was washed with methanol (10 g). To the combined filtrate HCl gas (90 g, 2.47 mol) was carefully introduced over 35 min. The internal temperature was maintained at 70–75° C., by external cooling. After complete addition of HCl gas, the mixture was cooled to 23° C. A turbid solution/suspension of L-tartaric acid (198 g, 1.32 mol) in water (120 g), and triethylamine (30 g, 0.30 mol), prepared at 30–35° C. in a separate vessel, was added to the solution, while the internal temperature was kept between 25–30° C. A pH of about 1 was observed. The resulting brownish solution was seeded with a few crystals of (1S,4R) methyl 4-aminocyclopent-2-ene-1-carboxylate L-tartrate. Triethylamine (116 g, 1.15 mol) was then added over 80 min. Each time 15 g of base was added to the solution, the solution was again seeded with a few crystals of (1S,4R) methyl 4-aminocyclopent-2-ene-1-carboxylate L-tartrate. Triethylamine base addition and seeding was continued until crystallization occurred. During the addition, the temperature was maintained below 40° C. After complete addition of the base the suspension was cooled to 23° C. and stirred for 2.5 h. The solid product ((1S,4R)-methyl 4-aminocyclopent-2-ene-1-carboxylate L-tartrate) was collected by filtration and washed with methanol (200 g).

Step 2:

Wet (1S,4R)-methyl 4-aminocyclopent-2-ene-1-carboxylate L-tartrate (285 g, about 0.95 mol) and di-tert-butyl carbonate (231.2 g, 1.06 mol) were suspended in methanol (124.2 g). Triethylamine (200.0 g, 1.98 mol) was added to the suspension, at 30–37° C. During addition of the triethylamine, strong gas evolution (CO$_2$) was observed. By the end of the addition, the reaction mixture became a clear, slightly yellowish solution. The solution was then stirred for 1.5 h without heating. Ammonium hydroxide 25% weight solution in water (14.4 g, 0.21 mol) was added and the solution was seeded with a few crystals of (1S,4R) methyl 4-[[(1,1,-dimethylethoxy)carbonyl]amino]cyclopent-2-ene-1-carboxylate. The solution was cooled to 0–5° C. and water (675 g) was added slowly, resulting in the formation of a white precipitate. The mixture was stirred for an additional 1 h at 0–5° C. and then filtered. The solid was washed with water (200 g) and dried at 35–40° C. under vacuum (<50 mbar) to yield the title product.

Yield: 212 g, 80%

EXAMPLE 7

Recrystallization

When the ee of the product of step 1 in Example 6 was below 97%, the following recrystallization was performed.

The wet product from step 1 of Example 6 (285 g) was slurried in water (320 g). The suspension was heated to 65° C. until all the solids were dissolved. 5 min after complete dissolution, occurred the solution was cooled to 55–60° C. and acetone (640 g) was added., resulting in precipitation of product. The reaction mixture was further cooled for 1.5 h to 0–5° C. and stirred for an additional 45 min at this temperature. The solid was collected by filtration and washed with methanol (80 g).

What is claimed:

1. A process for preparing a Compound of formula

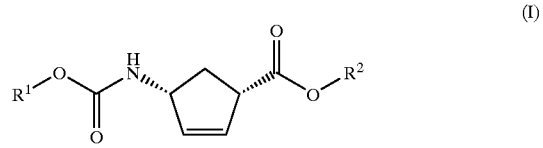

(I)

wherein

R$^1$ and R$^2$ are independently selected from the group consisting of hydrogen, alkyl, cycloalkyl, aryl, substituted aryl and aralkyl;

comprising reacting (±)2-azabicyclo[2.2.1]hept-5-en-3-one of formula (II)

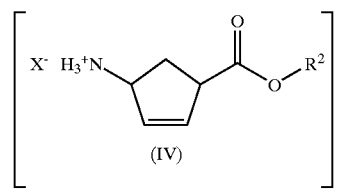

(II)

with an alcohol of formula (III), R$^1$OH, wherein R$^1$ is as described above, and a non-aqueous acid, to form the corresponding Compound of formula (IV), wherein X is the corresponding acid anion;

(IV)

reacting the Compound of formula (IV) with L-tartaric acid and a tertiary amine, to form the corresponding Compound of formula (V);

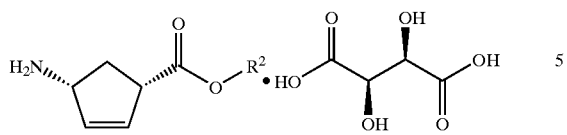
(V)

suspending the Compound of formula (V) in an organic solvent, and treating with a Compound of formula (VI), $(R^1OCO)_2O$, or a Compound of formula (VII), $R^1OC(O)Y$, wherein Y is chlorine or bromine and wherein $R^1$ is as set forth above, in the presence of a base, to form the corresponding Compound of formula (I).

2. A process for producing a compound of formula (I),

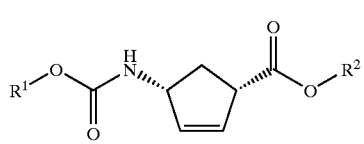
(I)

wherein
$R^1$ and $R^2$ are independently selected from the group consisting of hydrogen, alkyl, cycloalkyl, aryl, substituted aryl and aralkyl;
comprising
reacting (±)2-azabicyclo[2.2.1]hept-5-en-3-one of formula (II)

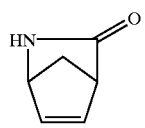
(II)

with a compound of formula (III), an alcohol represented by the formula $R^1OH$, wherein $R^1$ is as described above, and a non-aqueous acid, to form the corresponding Compound of formula (IV), wherein X is the corresponding acid anion;

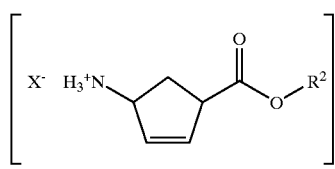
(IV)

reacting the compound of formula (IV) with D-tartaric acid and a tertiary amine, to form the corresponding compound of formula (VIII);

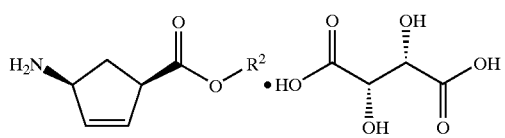
(VIII)

collecting the compound of formula (VIII) by filtration;

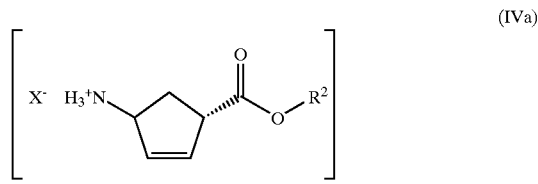
(IVa)

treating the filtrate containing the compound of formula (IVa) with L-tartaric acid and a tertiary amine, to form the corresponding compound of formula (V);

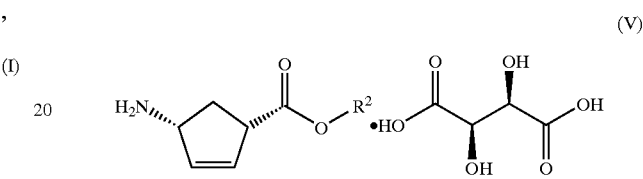
(V)

suspending the Compound of formula (V) in an organic solvent, and treating with a Compound of formula (VI), $(R^1OCO)_2O$, or a Compound of formula (VII), $R^1OC(O)Y$, wherein Y is chlorine or bromine and wherein $R^1$ is as set forth above, in the presence of a base, to form the corresponding Compound of formula (I).

3. The process of claim 1, wherein $R^1$ is tert-butyl and $R^2$ is methyl.

4. The process of claim 2, wherein $R^1$ is tert-butyl and $R^2$ is methyl.

5. The process of claim 3, wherein the non-aqueous acid is gaseous hydrochloric.

6. The process of claim 4, wherein the non-aqueous acid is gaseous hydrochloric.

7. The process of claim 3, wherein the L-tartaric acid is present in an amount in the range of 0.4–2.2 eq.

8. The process of claim 4, wherein the D-tartaric acid is present in an amount in the range of 0.4–2.2 eq.

9. The process of claim 3, wherein the tertiary amine is triethylamine.

10. The process of claim 4, wherein the tertiary amine is triethylamine.

11. The process of claim 3, wherein when the compound of formula (IV) is treated with a tertiary amine, the tertiary amine is present in an amount sufficient to adjust the pH to between about 1–5.

12. The process of claim 4, wherein when the compound of formula (IV) is treated with a tertiary amine, the tertiary amine is present in an amount sufficient to adjust the pH to between about 1–5.

13. The process of claim 3, wherein when the compound of formula (V) is suspended in an organic solvent, the organic solvent is an alcohol of formula (III).

14. The process of claim 4, wherein when the compound of formula (V) is suspended in an organic solvent, the organic solvent is an alcohol of formula (III).

15. The process of claim 3, wherein when the compound of formula (V) is reacted in the presence of a base, the base is triethylamine, present in an amount equal to at least 2 equivalents.

16. The process of claim 4, wherein when the compound of formula (V) is reacted in the presence of a base, the base is triethylamine, present in an amount equal to at least 2 equivalents.

17. A process for preparing a compound of formula (I)

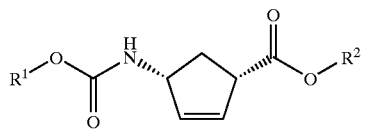
(I)

wherein

R$^1$ and R$^2$ are independently selected from the group consisting of hydrogen, alkyl, cycloalkyl, aryl, substituted aryl and aralkyl;

comprising reacting a Compound of formula (IV),

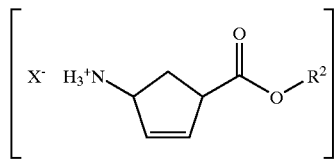
(IV)

wherein X is an acid anion of an acid and R$^2$ is as set forth above, with L-tartaric acid and a tertiary amine, to form the corresponding Compound of formula (V);

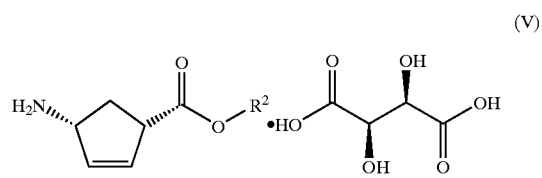
(V)

suspending the Compound of formula (V) in an alcohol of formula (III), R$^1$OH, wherein R$^1$ is as set forth above, and treating with a Compound of formula (VI), (R$^1$OCO)$_2$O, or a Compound of formula (VII), R$^1$OC(O)Y, wherein Y is chlorine or bromine and wherein R$^1$ is as set forth above, in the presence of a tertiary amine, to form the corresponding Compound of formula (I).

18. A compound of formula (V)

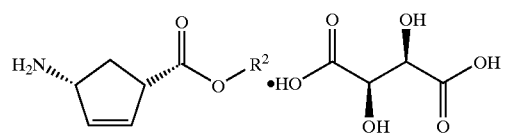
(V)

wherein R$^2$ is selected from the group consisting of hydrogen, alkyl, cycloalkyl, aryl, substituted aryl and aralkyl.

19. A compound of formula (V)

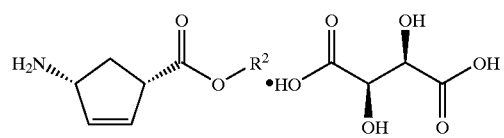
(V)

wherein R$^2$ is methyl.

* * * * *